US00PP11315P

United States Patent [19]

Verwer

[11] Patent Number: Plant 11,315

[45] Date of Patent: Mar. 28, 2000

[54] DAHLIA PLANT NAMED 'GALLERY SINGER'

[75] Inventor: Aad Verwer, Lisse, Netherlands

[73] Assignee: Fa. Gebr. Verwer, Lisse, Netherlands

[21] Appl. No.: 09/026,009

[22] Filed: Feb. 19, 1998

[30] Foreign Application Priority Data

Apr. 7, 1997 [NL] Netherlands ..... DHL79

[51] Int. Cl.[7] ..... A01H 5/00

[52] U.S. Cl. ..... Plt./321

[58] Field of Search ..... Plt./321

[56] References Cited

U.S. PATENT DOCUMENTS

P.P. 10,499 7/1998 Verwer ..... Plt./321

OTHER PUBLICATIONS

GTITM UPOVROM Citation for 'Gallery Singer' as per NL PBR DHL0079; Apr. 7, 1997.

*Primary Examiner*—Howard J. Locker
*Assistant Examiner*—Kent L. Bell
*Attorney, Agent, or Firm*—Christie, Parker & Hale, LLP

[57] ABSTRACT

A compact growing, continuously flowering perennial dahlia plant producing dark red flowers.

1 Drawing Sheet

BACKGROUND OF THE INVENTION

The present invention relates to a new and distinct variety of *Dahlia hybrida* known by the varietal denomination 'Gallery Singer'.

'Gallery Singer' is a cross between a variety known as 'Gallery Vermeer' (U.S. Plant Pat. No. 10,499) as seed parent and an unnamed, undistributed seedling as pollen parent.

SUMMARY OF THE INVENTION

The new variety is a dahlia plant with low growing habit which produces attractive dark red flowers against a background of abundant medium green foliage. The continuous flowering perennial plant is compact and suitable for use as a pot plant and for outdoor gardens. Inflorescences are compact and extend above the foliage borne on relatively short peduncles. Plant height is about 25 cm. Roots of cuttings of the new variety are initiated in about 5 days at 20° C. and a rooted cutting is produced in about 14 days at 20° C. The rooting habit is such that fine roots are produced first and then become fleshy. Among the traits possessed by the new variety which in combination distinguish it from other varieties known to the inventor are its compact plant habit, flower color, and continuous flowering during the growing season.

Asexual reproduction by cuttings of the new variety in The Netherlands has demonstrated that the combination of characteristics as described herein for 'Gallery Singer' are firmly fixed and are retained through successive generations of asexual reproduction.

COMPARISON WITH THE SEED PARENT

'Gallery Vermeer' produces orange/yellow ray florets and the new variety produces dark red ray florets.

BRIEF DESCRIPTION OF ILLUSTRATION

The accompanying color photographic illustration shows a typical plant of the new variety in colors as nearly true as possible with an illustration of this type. The illustration depicts growth habit, flower position relative to leaves and flower color.

DESCRIPTION OF THE NEW VARIETY

In the following description, color references are to The Royal Horticultural Society Colour Chart, where color values refer to color plate numbers in this chart.

The following observations are of plants described and grown in The Netherlands under greenhouse and outdoor conditions which approximate those generally used in commercial practice.

'Gallery Singer' has not been observed under all possible environmental conditions. The phenotype may vary with variations in environment such as temperature, light intensity, day length and cultural conditions.

Growing conditions: Useful growing conditions include day temperatures of about 15° to 22° C. and night temperature about 10° to 15° C. with normal daylight about 14 hours. Plants grow normally June to September in The Netherlands. No growth regulator treatments are required.

Plant:

*Plant shape.*—Rounded.
*Growth habit.*—Spreading.
*Height.*—About 25 cm.
*Growth rate.*—Rapid.
*Branching characteristics.*—Freely branching.
*Vigor.*—Vigorous.
*Crop time.*—About 60 days.
*Hardiness.*—Plants are winter hardy to 0° C.
*Disease resistance.*—Similar to the species.

Foliage:

*Arrangement.*—Opposite.
*Type.*—Compound and single.
*Leaves.*—Quantity of leaves: Many. Arrangement and size: Opposite, simple or compound, compound leaves have either three or five leaflets; single leaves about 6 cm long, about 4 cm wide; compound leaves about 15 cm long, about 11 cm wide Shape: Ovate. Tip: Acute, acuminate. Base: Acute. Attachment: Stalked, petioled.
*Petiole length.*—At base about 50 mm.
*Margin.*—Dentate.
*Texture.*—Leathery.
*Pubescence upper side and underside.*—None.
*Color.*—Young foliage: Upper side near 137B; under side near 191A. Mature foliage: Upper side near 139A; under side near 147B. Petiole: Near 191C.

Venation: Upper side near 139A; under side near 191C.

*Venation pattern.*—Pinnate.

Flower

*Habit.*—Recurrent, continuous during season.

*Form.*—Decorative.

*Natural flowering season.*—Summer and Autumn.

*Quantity of flowers per stem.*—Usually 1.

*Diameter.*—About 70 mm.

*Depth.*—About 40 mm.

*Longevity on plant.*—About 14 to 20 days.

*Longevity as cut flower.*—About 6 days.

*Persistent or self-cleaning.*—No self-cleaning.

*Fragrance.*—None.

*Ray florets.*—Appearance: Satiny. Texture: Smooth. Arrangement: In circles around center. Shape: Ovate. Margin: Entire. Tip: Acute. Length: About 30 mm. Width: About 12 mm. Color: When opening: Near 53A. Upper side: Near 53A. Under side: Near 46B. Fading to: Near 18A. After Senescence: Near 22A.

*Disc florets.*—Number: About 10. Length: About 7 mm. Color: Near 7A. Shape: Cylindric.

*Peduncle or flower stem.*—Length: About 15 cm. Color Near 183A. Strength: Strong Angle: Erect. Pubescence: None.

*Bud.*—Length: About 10 mm. Diameter: About 10 mm. Shape: Globular. Rate of opening: About 10 to 14 days. Color: Near 151B.

*Sepals.*—Appearance: Satiny. Texture: Smooth. Arrangement: In circle around stem Number: About 20. Length: About 1.9 cm. Width: About 1.5 cm. Shape: Ovate. Margin: Entire. Tip: Acute. Color: Upper side near 137C; under side near 137A.

*Calyx.*—Small.

*Stamens.*—Number: Many. Anther shape: Long, pointed. Anther size: Small. Anther color: Near 14A. Pollen color: Near 17B.

*Pistils.*—Number: Many. Stigma shape: Divided, two. Stigma color: Near 14A. Style color: Near 154B. Style length: About 2 mm. Ovary number: 1 per pistil.

I claim:

1. A new and distinct dahlia plant of the variety substantially as shown and described.

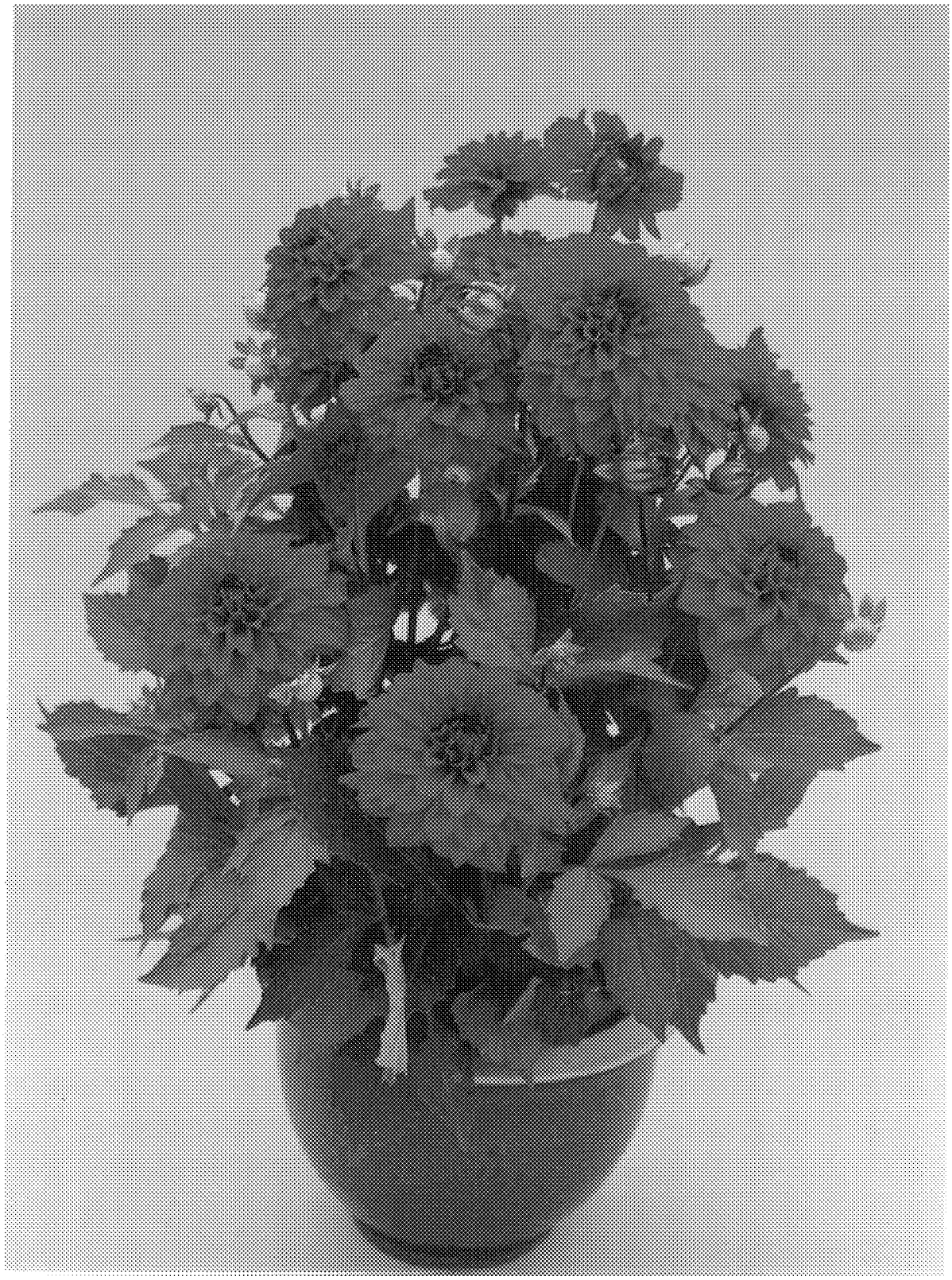

* * * * *